US012678261B2

(12) United States Patent
Forstein et al.

(10) Patent No.: US 12,678,261 B2
(45) Date of Patent: Jul. 14, 2026

(54) SYSTEM AND METHOD FOR DETECTING A POTENTIAL COLLISION BETWEEN A BONE AND AN END-EFFECTOR

(71) Applicant: CUREXO, INC., Seoul (KR)

(72) Inventors: Micah Forstein, Fremont, CA (US);
Amit Sandhu, Fremont, CA (US)

(73) Assignee: CUREXO, INC., Seoul (KR)

( * ) Notice: Subject to any disclaimer, the term of this patent is extended or adjusted under 35 U.S.C. 154(b) by 324 days.

(21) Appl. No.: 18/284,092

(22) PCT Filed: Mar. 21, 2022

(86) PCT No.: PCT/US2022/021116
§ 371 (c)(1),
(2) Date: Sep. 26, 2023

(87) PCT Pub. No.: WO2022/204010
PCT Pub. Date: Sep. 29, 2022

(65) Prior Publication Data
US 2024/0173096 A1      May 30, 2024

Related U.S. Application Data

(60) Provisional application No. 63/166,293, filed on Mar. 26, 2021.

(51) Int. Cl.
*A61B 90/00*          (2016.01)
*A61B 34/10*          (2016.01)
(52) U.S. Cl.
CPC .............. *A61B 90/37* (2016.02); *A61B 34/10* (2016.02); *A61B 2034/104* (2016.02); *A61B 2034/105* (2016.02)

(58) Field of Classification Search
CPC ......... A61B 90/00; A61B 90/37; A61B 90/36; A61B 90/361; A61B 34/10; A61B 34/76
See application file for complete search history.

(56) References Cited

U.S. PATENT DOCUMENTS

| | | |
|---|---|---|
| 2009/0192524 A1 | 7/2009 | Itkowitz et al. |
| 2019/0069962 A1* | 3/2019 | Tabandeh ............... A61B 90/39 |
| 2020/0281656 A1* | 9/2020 | Torabi .................... A61B 34/37 |

FOREIGN PATENT DOCUMENTS

| | | |
|---|---|---|
| WO | 2016044574 A1 | 3/2016 |
| WO | 2017087371 A1 | 5/2017 |

(Continued)

OTHER PUBLICATIONS

Int'l Search Report for PCT/US2022/021116, dated Jun. 30, 2022.

*Primary Examiner* — Christopher J Beccia
(74) *Attorney, Agent, or Firm* — Bridgeway IP Law Group, PLLC; Jihun Kim

(57) ABSTRACT

A method of detecting a potential collision between an end-effector and bystander anatomy is provided. A cut-file or a representation of an implant is registered to a position of a first bone, the registered cut-file defining at least one orientation for an end-effector axis to assume while physically modifying the first bone. Imaging data of bystander anatomy is registered to a position of the bystander anatomy. The at least one orientation of the end-effector axis as defined in the registered cut-file is calculated in a computer if it has a spatial overlap with the registered imaging data to detect the potential collision. A portion of the registered representation can also projected along an axis with the projection used to determine possible collisions and if so provide the user with options.

7 Claims, 9 Drawing Sheets

(56)          References Cited

FOREIGN PATENT DOCUMENTS

WO          2019245865  A1    12/2019
WO          2020190832  A1     9/2020

* cited by examiner

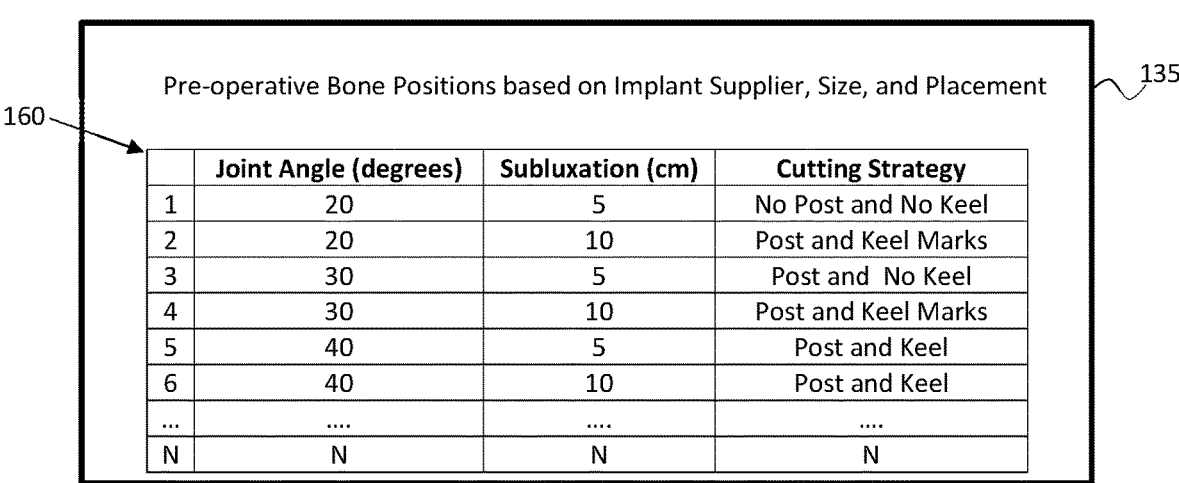

Pre-operative Bone Positions based on Implant Supplier, Size, and Placement ⟋135

160

|   | Joint Angle (degrees) | Subluxation (cm) | Cutting Strategy |
|---|---|---|---|
| 1 | 20 | 5 | No Post and No Keel |
| 2 | 20 | 10 | Post and Keel Marks |
| 3 | 30 | 5 | Post and  No Keel |
| 4 | 30 | 10 | Post and Keel Marks |
| 5 | 40 | 5 | Post and Keel |
| 6 | 40 | 10 | Post and Keel |
| ... | .... | .... | .... |
| N | N | N | N |

FIG. 6A

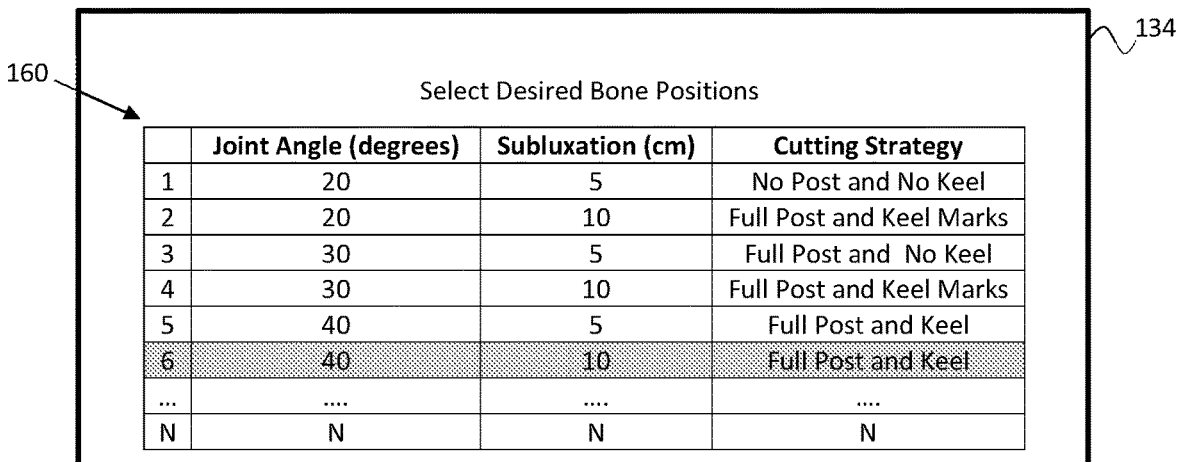

⟋134

160

Select Desired Bone Positions

|   | Joint Angle (degrees) | Subluxation (cm) | Cutting Strategy |
|---|---|---|---|
| 1 | 20 | 5 | No Post and No Keel |
| 2 | 20 | 10 | Full Post and Keel Marks |
| 3 | 30 | 5 | Full Post and  No Keel |
| 4 | 30 | 10 | Full Post and Keel Marks |
| 5 | 40 | 5 | Full Post and Keel |
| 6 | 40 | 10 | Full Post and Keel |
| ... | .... | .... | .... |
| N | N | N | N |

FIG. 6B

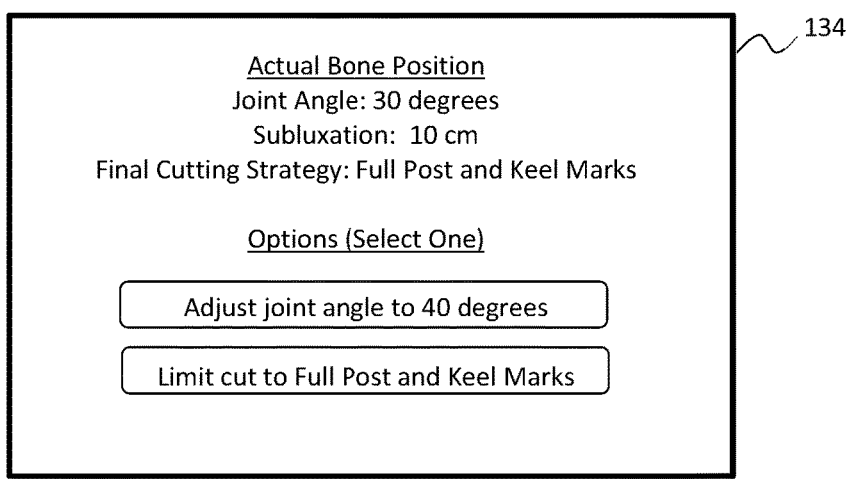

⟋134

Actual Bone Position
Joint Angle: 30 degrees
Subluxation:  10 cm
Final Cutting Strategy: Full Post and Keel Marks Options (Select One)

Adjust joint angle to 40 degrees

Limit cut to Full Post and Keel Marks

FIG. 6C

SYSTEM AND METHOD FOR DETECTING A POTENTIAL COLLISION BETWEEN A BONE AND AN END-EFFECTOR

RELATED APPLICATIONS

This application claims priority benefit of U.S. Provisional Application Ser. No. 63/166,293, filed Mar. 26, 2021; the contents of which are hereby incorporated by reference.

TECHNICAL FIELD

The present invention generally relates to computer-assisted surgery, and more particularly to the positioning of one or more bones to provide enough clearance for a computer-assisted surgical device to execute a surgical plan associated with the computer-assisted surgery.

BACKGROUND

Orthopedic computer-assisted surgical (CAS) system is gaining popularity as a tool to pre-operatively plan and precisely execute the surgical plan to ensure an accurate final position and orientation of a prosthetic within a patient's bone that can improve long term clinical outcomes and increase the survival rate of a prosthesis. A conventional CAS procedure begins with the generation of the surgical plan using planning software. The planning software generates a three dimensional (3-D) model of the patient's bony anatomy from a computed tomography (CT) or magnetic resonance imaging (MRI) image dataset of the patient. A set of 3-D computer aided design (CAD) models of the manufacturer's prosthesis are pre-loaded in the software that allows the user to test the components of a desired prosthesis to the 3-D model of the bony anatomy so as to determine the best fit, fill, position, and/or orientation of the prosthesis to the bone. Once the user designates the desired placement for the prosthesis relative to the bone, the surgical plan is saved and includes a set of instructions for a CAS device to modify the bone to receive the selected prosthesis in the desired position and orientation (POSE). The plan is then transferred to the CAS system in the operating room (OR) to assist the surgeon intra-operatively in executing the plan.

To perform a joint replacement procedure with a CAS system, the correct positioning of the anatomy with respect to the CAS device is critical to accurately execute the plan in a time efficient manner. Currently, a moveable base of the CAS device is manually maneuvered next to the target anatomy. The surgical plan is then registered or mapped to the POSE of the anatomy with respect to a coordinate system of the CAS system such that the CAS device knows where to execute the plan on the anatomy. After registration, the CAS system may execute a software routine to determine if an end-effector of the CAS device can successfully execute the surgical plan on the anatomy. The software routine checks if the parameters (e.g., points, paths, or boundaries) defined in the set of instructions and now registered to the POSE of the anatomy is reachable by the end-effector. If any of the parameters are outside the reach of the end-effector, the patient needs to be unfixed from the robot, the robot needs to be re-positioned, and the anatomy re-fixed to the robot, all of which costs a considerable amount of time.

The primary problem with the current procedure is that there is limited feedback, either during planning or in the OR, for the optimal position of the anatomy relative to the CAS device before the patient is fixed. The same is true for a CAS system that utilizes a tracking system in lieu of fixation to track the position of the anatomy relative to the CAS device in real-time. If at any time the bones move out of reach of the end-effector then the CAS device cannot execute the plan. The user currently has no feedback as to the best position for the tracked anatomy relative to the CAS device. All of these problems can greatly increase the operating time.

Another problem with the limited feedback of a conventional procedure is the prospect of a potential collision of the end-effector with an opposing bone. For example, with reference to FIGS. 1A and 1B, in total knee arthroplasty (TKA) both the distal femur "F" and proximal tibia "T" are modified to repair the joint, where an end-effector 120 may inadvertently collide with the femur "F" while modifying the tibia "T". The tibia "T" is modified to receive a tibial implant 100 as shown in FIG. 1A. The tibial implant 100 includes a tibial tray 102, a post 104, and a keel 106, where the keel 106 has wings laterally from the post 104. The tibia "T" is therefore modified with a planar surface 108, and a post hole 110 and keel holes 112 to receive the tibial implant 100. Prior to any modification, the user has to consider the position of the bones with respect to each other, otherwise one of the bones may interfere with the movements of the end-effector 120 while the end-effector modifies the other bone. As shown in FIG. 1B, an end-effector 120 is modifying a proximal tibia. The end-effector 120 includes a tool 122 having a distal end that removes material from a bone, a sleeve 124 supporting a shaft of the tool 122, and a coupler 126 for coupling the end-effector 120 to a robot. During the procedure while the end-effector 120 is moving to modify the tibia "T", the end-effector 120 may orient into a position causing an inadvertent collision with the femur "F". The collision is shown in the circled region of FIG. 1B. This is most likely to occur at certain end-effector 120 orientations such as when the end-effector 120 is forming the post hole 110 or keel holes 112 keel holes in the tibia "T". A collision of the end-effector 120 with an opposing bone will trigger a "force freeze", which is a safety mechanism to pause the movement of the end-effector 120 when a force sensor associated with the robotic device senses an unexpected force or a force above a specified threshold on the end-effector 120. Once a "force freeze" is triggered, the femur "F" can be safely moved to permit the end-effector 120 to finish modifying the tibia "T". Alternatively, and depending on the amount of modification that has already occurred, the user may stop the procedure and finish the modifications to the tibia "T" with manual instrumentation. Both of these outcomes increase the overall surgical time and there is currently no method to aid the surgeon in positioning the bones prior to the bone modifications to best avoid these collisions and "force freezes."

Thus, there exists a need for a system and method to assist a user in positioning two or more bones relative to one another to provide enough clearance between the bones for a CAS device to execute a surgical plan and thereby overcome the above-noted limitations of the prior art. There is a further need for one or more alignment devices to assist with this positioning.

SUMMARY OF THE INVENTION

A method of detecting a potential collision between an end-effector and bystander anatomy is provided. A cut-file or a representation of an implant is registered to a position of a first bone, the registered cut-file defining at least one orientation for an end-effector axis to assume while physically modifying the first bone. Imaging data of bystander anatomy is registered to a position of the bystander anatomy. The at least one orientation of the end-effector axis as defined in the registered cut-file is calculated in a computer if it has a spatial overlap with the registered imaging data to detect the potential collision. Potential collisions can include: a) an axis of a portion of the registered representation; or b) a projected cross-section of the portion of the registered representation.

A computerized method of collision avoidance between an end-effector and bystander anatomy during a surgical procedure performed by a computer-assisted surgical (CAS) system is also provided. A representation of an implant is registered to a position of a first bone. Imaging data of bystander anatomy is registered to a position of the bystander anatomy. A portion of the registered representation is projected along an axis, in which the axis represents an orientation of the end-effector when cutting at least a portion of the first bone. The projection is determined as to collision with the registered imaging data. If the projection collides, the user is presented with options that include at least one of: a) physically moving at least one of the first bone or the bystander anatomy; b) limiting a number cuts to the first bone by the end-effector to preclude contact between the end effector and the bystander anatomy; or c) a combination thereof.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Dimensions of components and features shown in the figures are generally chosen for convenience and clarity of presentation and are not necessarily shown to scale. The figures are listed below.

FIG. 3A depicts a potential collision, and FIG. 3B depicts collision avoidance.

FIG. 6A depicts a pre-operative graphical user interface displaying a table of potential joint angles, subluxations, and cutting strategies for a given joint angle and subluxation to assist a user in positioning the bones in the OR prior to a joint replacement procedure.

FIG. 6B depicts an intra-operative graphical user interface displaying a table of potential joint angles, subluxations, and cutting strategies for a given joint angle and subluxation to assist a user in positioning the bones in the OR prior to a joint replacement procedure.

FIG. 6C depicts an intra-operative graphical user interface displaying the actual position of the bones in the OR and providing options on how to proceed based on the actual position of the bone.

FIG. 8A is top perspective view thereof, FIG. 8B is top view thereof, and FIG. 8C is a bottom perspective view thereof.

DETAILED DESCRIPTION

Figures 1A, 1B:
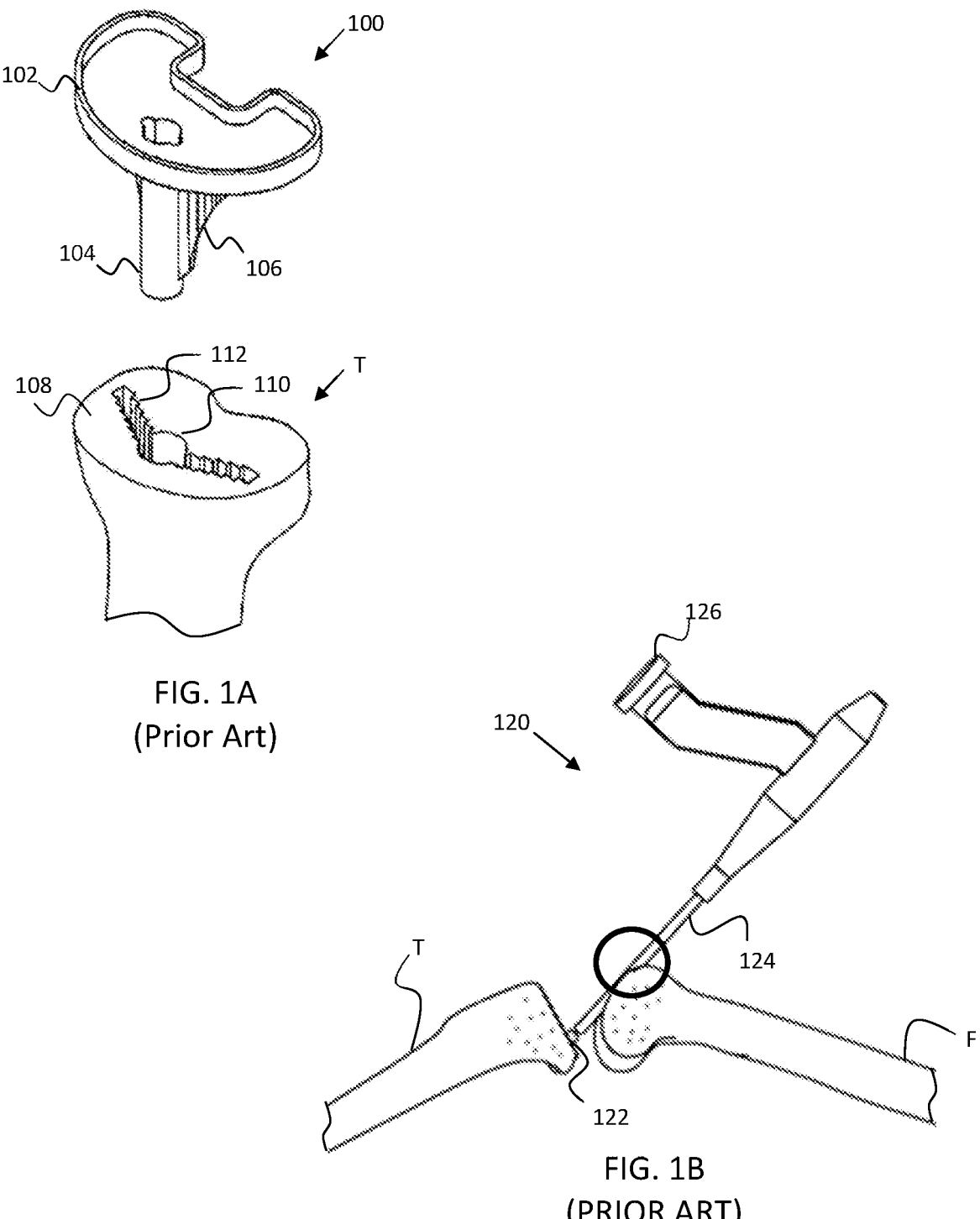
FIG. 1A depicts a prior art tibial implant and a prepared tibial plateau to receive the tibial implant in a planned position.
FIG. 1B depicts a prior art scenario of an end-effector modifying a first bone and inadvertently colliding with an opposing bone.

The present invention has utility in assisting a user in positioning two or more bones relative to one another to provide enough clearance between the bones for a computer-assisted surgical (CAS) device to execute a surgical plan. The present invention will now be described with reference to the following embodiments. As is apparent by these descriptions, this invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment may be deleted from the embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations, and variations thereof.

Furthermore, it should also be appreciated that although the systems and methods described herein provide examples with reference to total knee arthroplasty, the systems and methods of the present invention may be applied to other computer-assisted surgical procedures involving other joints in the body. By way of example but not limitation, the system and method of the present invention may be applied to the joints of the hip, ankle, shoulder, spine, jaw, elbow, wrist, hands, fingers, feet, toes, etc., as well as revision of initial repair or replacement of any joints or bones.

As used herein, the term "pre-operative bone data" refers to data used to plan a surgical procedure prior to making modifications to the bone. The pre-operative bone data may include one or more of the following: an image data set of the bone (e.g., an image data set acquired via computed tomography (CT), magnetic resonance imaging (MRI), ultrasound, x-ray, laser scan, etc.), a virtual generic model of the bone, a physical model of the bone, a virtual patient-specific model of the bone generated from an image data set of the bone, a set of data collected directly on the bone intra-operatively (commonly used with imageless computer-assist devices), etc.

As used herein, the term "digitizer" refers to a device capable of measuring, collecting, recording, or designating the location of physical points or structures in three-dimensional space. By way of example but not limitation, the "digitizer" may be: a "mechanical digitizer" having passive links and joints, such as the high-resolution electro-mechanical sensor arm described in U.S. Pat. No. 6,033,415 (which U.S. patent is hereby incorporated herein by reference); a non-mechanically tracked digitizer probe (e.g., optically tracked, electromagnetically tracked, acoustically tracked, and equivalents thereof) as described for example in U.S. Pat. No. 7,043,961 (which U.S. patent is hereby incorporated herein by reference); an end-effector of a robotic device; or a laser scanner.

As used herein, the term "digitizing" refers to collecting, measuring, designating and/or recording the location of physical points or structures in space using a digitizer.

As used herein, a "cut-file" refers to a software file having a set of instructions to automatically, semi-automatically, or haptically control a CAS device (e.g., a robot). The set of instructions illustratively include cut paths (e.g., the paths the end-effector is directed to remove/cut bone and orientations of an end-effector axis while being directed along a cut path), points, virtual boundaries, velocities, end-effector axis orientations, accelerations, spindle speeds, feed rates, and any combination thereof to automatically, semi-automatically, or haptically control the CAS device.

As used herein, the term "registration" refers to: the determination of the spatial relationship between two or more objects; the determining of a coordinate transformation between two or more coordinate systems associated with those objects; and/or the mapping of an object onto another object. Examples of objects routinely registered in an operating room (OR) illustratively include: CAS systems/devices; anatomy (e.g., bone); pre-operative bone data (e.g., 3-D virtual bone models); surgical planning data (e.g., an implant model positioned relative to pre-operative bone data, a cut-file defined relative to an implant model and/or pre-operative bone data, virtual boundaries defined relative to an implant model and/or pre-operative bone data, virtual planes defined relative to an implant model and/or pre-operative bone data, or other cutting parameters associated with or defined relative to an implant model and/or the pre-operative bone data); and any external landmarks (e.g., a tracking array affixed to a bone, an anatomical landmark, a designated point/feature on a bone, etc.) associated with the bone (if such landmarks exist). Methods of registration known in the art are described in U.S. Pat. Nos. 6,033,415; 8,010,177; 8,036,441; and 8,287,522; and U.S. Patent Application Publication 2016/0338776, which patents and publications are hereby incorporated herein by reference.

As used herein, the term "real-time" refers to the processing of input data within milliseconds, such that calculated values are available within 2 seconds of computational initiation.

As used herein, the term "optical communication" refers to wireless data transferred via modulated infrared or visible light as described in U.S. Patent Application Publication No. 2017/0245945 assigned to the assignee of the present application and incorporated by reference herein in its entirety.

As used herein, the term "computer-assisted surgical (CAS) device" refers to a device requiring a computer to assist in executing a surgical procedure. The term "computer-assisted surgical (CAS) system" refers to a system comprising at least one CAS device and any additional devices (e.g., another CAS device or a device not requiring a computer to function) to assist in executing a surgical procedure. Examples of a CAS device illustratively include a tracking system, automated or semi-automated hand-held devices, automated or semi-automated serial-chain robots, haptic serial chain robots, parallel robots, or master-slave robots, as described in U.S. Pat. Nos. 5,086,401; 7,206,626; 8,876,830; and 8,961,536; and U.S. Patent Application Publication No. 2013/0060278, which patents and patent application are incorporated herein by reference. An example of a CAS system may include: a) a CAS device (e.g., a tracking system and a serial-chain robot) and any other device or hardware that may not require the use of a computer to function (e.g., a tracked instrument, bone pins, a rongeur, an oscillating saw, a rotary drill, etc.); b) two or more CAS devices; or c) two or more CAS devices and any other device or hardware that may not require the use of a computer to function. A particular CAS system equipped to execute embodiments of the inventive method described herein is provided below.

Embodiments of the invention provide various systems, methods, and devices to assist a user in positioning two or more bones relative to one another to provide enough clearance between the bones for a CAS device to execute a surgical plan. The systems, methods, and devices may provide feedback or assistance to position the bones. Once the bones are positioned, the potential for an end-effector of a CAS device to collide with an opposing bone (referred to hereinafter as an "end-effector collision") is minimized thereby reducing operating times and improving the workflow of the procedure. Specific systems and methods will now be described with reference to the figures.

Feedback Using Registered Bone Position and Surgical Plan

Embodiments of an inventive CAS system and method for providing visual feedback to assist a user in positioning the bones may generally include the following. A section view of an implant feature (e.g., tibial post), in a planned position relative to a first bone model (e.g., tibia bone model), is projected normal to its cutting axis (i.e., the axis of the end-effector as the end-effector cuts the bone to form the implant feature) as defined by the registration of the first bone. The section view of the implant feature is projected through bystander anatomy. Bystander anatomy in the context of the present invention includes ligaments, nerves, muscles, or bones associated with the joint. While less invasive joint replacement procedures retain one or more of these tissues in place while the first bone of the joint is resurfaced to receive an implant, in conventional total knee arthroplasty (TKA) as routinely performed, some of these tissues are displaced to leave the mating bone of the joint in place and possible one or more ligaments (e.g., the posterior cruciate ligament). For visual clarity the bystander anatomy is shown in the inventive figures as the second bone of the joint and is registered with a second bone model (e.g., femur bone model). A view of the second bone model registered to the physical second bone may be displayed on a display (e.g., a monitor). If the second bone is intersecting the cross sectional view, then repositioning (e.g., through subluxation) of the first bone may be required, or the user may choose to skip the cutting of the implant feature with the CAS system due to the intersection. It is appreciated that the collision avoidance methods of the present invention are equally applicable to these various recited bystander anatomy types. Computational techniques for robotic collision avoidance are known to the art. D. Fox et al. IEEE Robotics & Automation Magazine 4.1 (1997): 23-33. While the present invention is further detailed with respect to an exemplary TKA procedure, it is appreciated that the methods and systems detailed herein are also applicable to a variety of surgical bone implants in both human and animal subjects.

Figure 2:
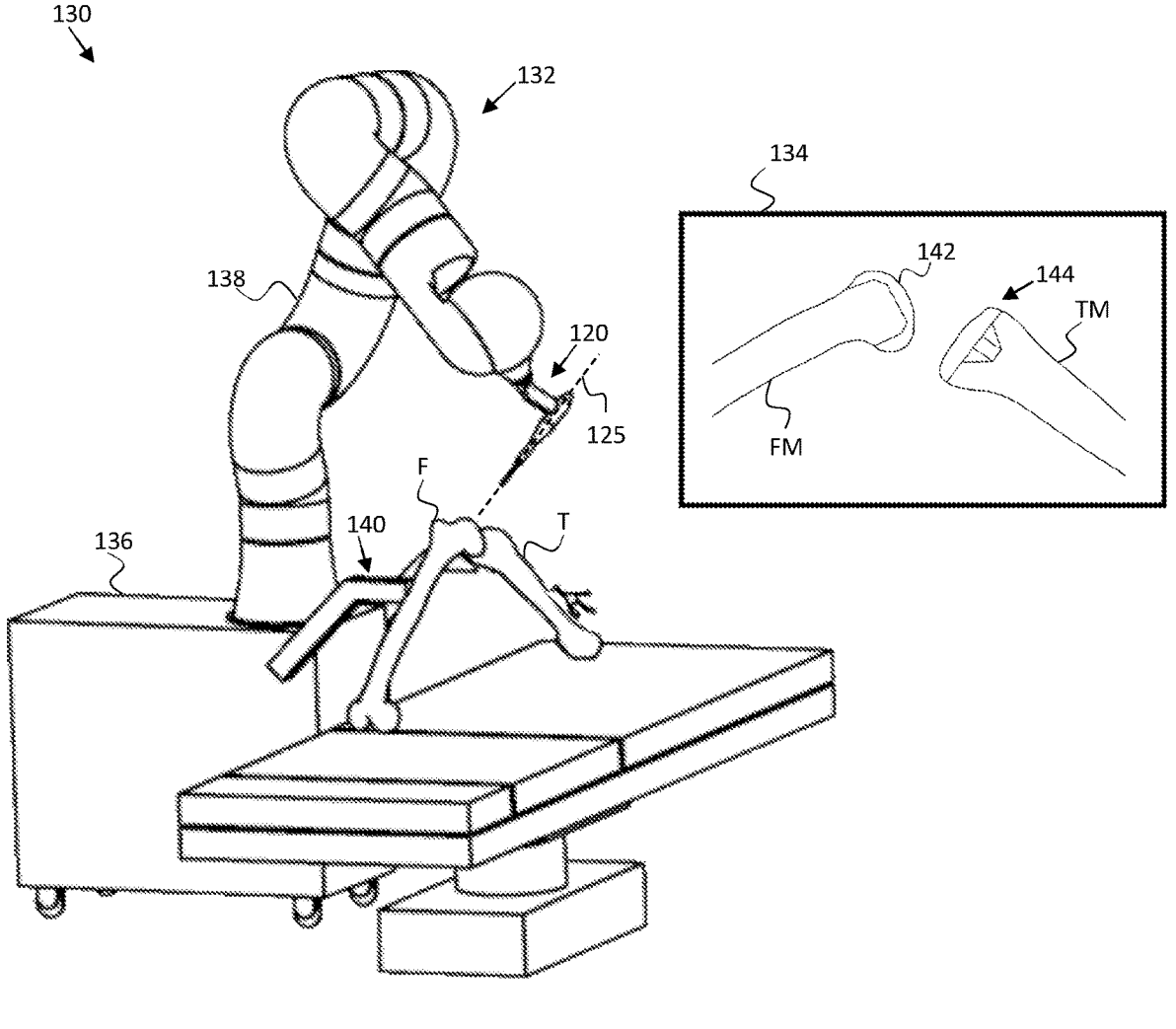
FIG. 2 depicts a robotic surgical system that provides visual feedback to a user to assist in positioning a pair of bones prior to a joint replacement procedure, including an inset magnification of the femur bone model 'FM' and tibia bone model 'TM' interface.
Figure 3A:
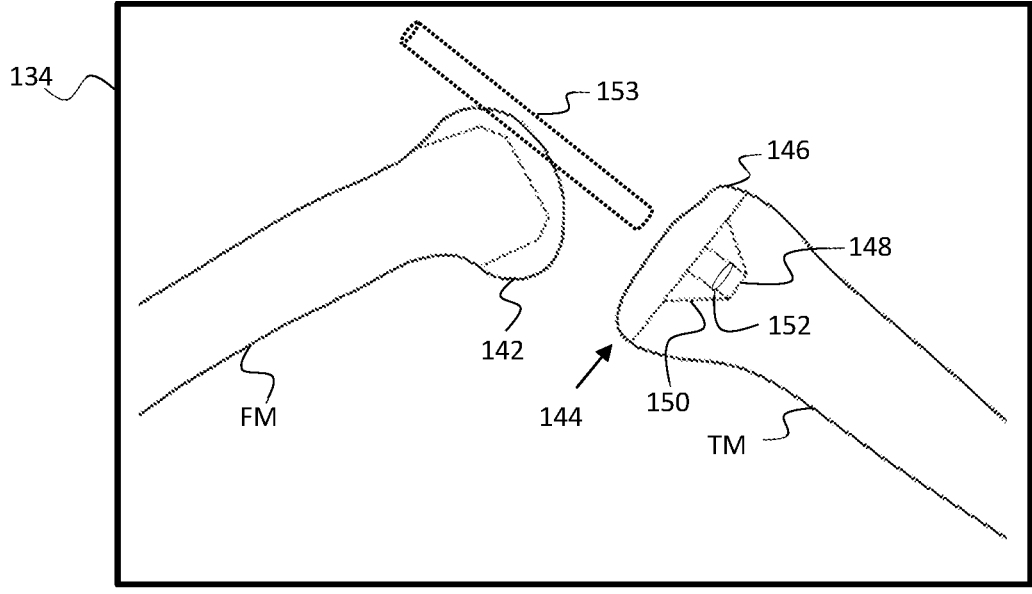
FIGS. 3A and 3B depict a graphical user interface displaying a femur bone model and a tibia bone model having a femoral implant model and a tibia implant model thereon, respectively, wherein a section view of a tibia implant feature is projected relative to the femur bone model to assess the potential for an end-effector collision, where
Figure 3B:
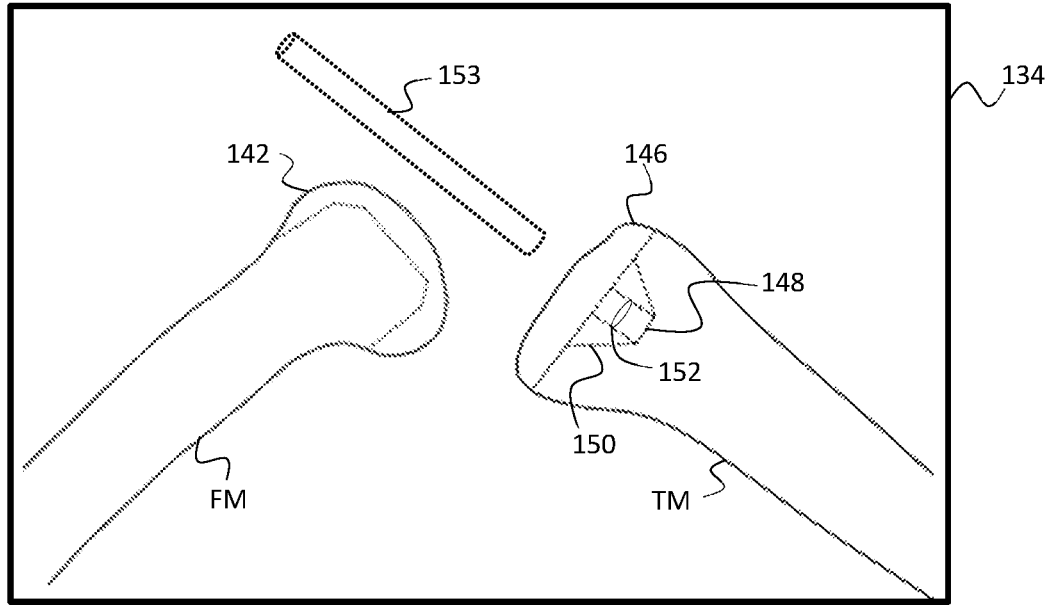

For example, with reference to FIGS. 2, 3A, and 3B, a system and method for providing visual feedback to assist a user in positioning a femur "F" and tibia "T" in the context of TKA are shown. FIG. 2 depicts a CAS system 130 including a surgical robot 132 and a monitor 134 for displaying a graphical user interface (GUI). The surgical robot 132 may include a base 136, a robotic arm 138 attached to the base 136, and an end-effector 120 coupled to a distal end of the robotic arm 136. The surgical robot 132 may further include one or more fixator arms 140 fixed, or removably assembled, to the base 136 to fix one or more bones (e.g., femur "F" and tibia "T") to the surgical robot 132. The CAS system may further include a pre-operative planning workstation, as shown in greater detail with respect to FIG. 11 and described below.

Embodiments of the method may begin by generating a surgical plan. Images of the patient's femur "F" and tibia "T" are obtained using CT, MRI, or other imaging modality that provides three-dimensional details about a given bone and surrounding bystander anatomy. The images are then uploaded in the pre-operative planning software for post processing, such as image segmentation, and to generate 3-D models of the femur "F" and tibia "T" (referred to hereinafter as femur bone model 'FM' and tibia bone model "TM). The planning software further includes a library of implant models (e.g., computer-aided design (CAD) models) for the user to choose a desired implant line, type, size, or combination of such factors. Various tools in the planning software permits the user to place one or more implant models relative to the 3-D bone models to designate the best fit, fill, or alignment for the final position of the implants on the bones. The positioning of the implant models relative to the 3-D bone models may be accomplished manually, semiautomatically, or automatically using the various tools in the planning software.

In particular embodiments, the pre-operative planning software includes best-fit algorithms to semi-automatically or automatically assist in positioning the implant models relative to the 3-D models of the bones of a patient by calculating the "best-fit", which relative to the other possible fits has absolute certainty in every instance as having less deviation than other fits generated. Geometric algorithms to numerically determine such set of parameters are conventional to the art as numerical optimization algorithms, that illustratively include the Gauss-Newton algorithm and linear regression analysis algorithms. Such numerical optimization algorithms calculate the difference between actual data points and data points of the modeling and minimizes the summation of differences for a given fit. In some best fit models, weighting is applied to certain areas where fit parameters are considered important. The best fit can be evaluated even when different types of models are used and is always the one with the least difference. *Numerical Recipes in C, The Art of Scientific Computing, Second Edition* (1992). The introductory part of Chapter 15 describes the basic tasks of best-fit algorithms (see page 656). Chapter 15.5 "Nonlinear Models" explains amongst others the numerical implementation of a Levenberg-Marquardt algorithm (pg. 683) that is suitable for non-linear geometry (functions) as for instance anatomical shapes and geometry.

Once the user is satisfied with the final implant placement, the surgical plan is saved and may be transferred or otherwise uploaded to the CAS system 130 located in the operating room (OR) if the planning computer is located outside the OR. The surgical plan may include the 3-D bone models and the desired position for the implant models relative to the 3-D bone models. The surgical plan may further include other operational information for executing the TKA procedure with a CAS device as further described with reference to FIG. 11 below.

In the operating room (OR), the patient is positioned on the OR table and prepared in a typical manner. Once the femur "F" and tibia "T" are exposed, each fixator arm 140 (one on each side of the surgical robot 132) is fixed to a bone. Each fixator arm 140 may include a series of rods joined by clamps that assemble to a pin installed in the bone. After the bones are fixed, the surgical plan is registered to each bone with respect to the CAS system 130 using registration techniques known in the art. Based on the registered position of the bones, the monitor 132 displays the 3-D model of the femur 'FM' and the 3-D model of the tibia 'TM' in their relative positions to one another as they are registered in the OR. It is appreciated that a bone not receiving an implant in a particular stage of the procedure is considered bystander anatomy that is to be avoided while preparing a first bone for implant revision or to receive an implant. The monitor 134 may further display the planned position of the femoral implant model 144 on the femur bone model 'FM', and the planned position of the tibial implant model 146 on the tibia bone model 'TM'. A tibial tray model 146, post model 148, and a keel model 150 of the tibia implant model 146 may also be displayed.

At this point, feedback (e.g., visual, audio, tactile, etc.) may be provided to the user to assess the potential for an end-effector collision to occur with the femur "F" while the end-effector 120 modifies parts of the tibia "T". In a specific embodiment, with reference to FIGS. 3A and 3B, a section view 152 (or cross-section view) of the post model 148 may be projected along an axis to create a projected section view 153 relative to the registered femur bone model 'FM'. The axis that the section view 152 is projected along may be an axis normal to the cutting axis (or normal to its crosssectional slice) of the section view 152, but more specifically is an axis representing the orientation of the tool 122 and/or sleeve 124 of the end-effector 120 while the end-effector 120 forms the post hole 110 in the tibia "T". Therefore, if the projected section view 153 intersects with the registered femur bone model 'FM', as shown in FIG. 3A, then there is a high likelihood that the end-effector 120 will collide with the femur "F" while forming the post hole 110 in the tibia "T".

The projected section view 153 may be shown on the monitor 134 to provide visual feedback as shown in FIGS. 3A and 3B, while in other embodiments, the projected section view 153 is not shown on the monitor 153 and the computer software internally computes if there is any intersection with the registered femur bone model 'FM' and subsequently provides other feedback to the user (e.g., an audible alert, tactile sensation) as further described below.

The projection of the section view 152 may be accomplished with traditional computer graphics software techniques. In a particular embodiment, the position of the section view 152 is identified and the coordinates of the section view 152 (which is in the coordinate frame of the registered tibia bone model 'TM') is transformed into the coordinate frame of the registered femoral bone model 'FM', wherein the section view 152 is then projected (or extruded) in the coordinate frame of the registered femoral bone model 'FM'. Alternatively, this may be accomplished by projecting (or extruding) the section view 152, while in the coordinate frame of the registered tibial bone model 'TM', to extend beyond the tibial bone model 'TM' by a distance sufficient to visualize any potential intersection with the registered femoral bone model 'FM'. If a collision is expected (as determined by the projected section view 153 intersecting with the registered femoral bone model 'FM'), the user may avoid the collision by either: a) re-positioning the bones (e.g., through subluxation of the tibia "T"); or b) choosing to skip one or more cuts to be made, particularly the cut associated with the formation of the post 110. If the user decides to re-position the bones, the bones are physically re-positioned and the above procedure repeated until the projection section view 153 no longer intersects with the registered femur bone model 'FM' as shown on the monitor 134 in FIG. 3B. It should be appreciated that the visual feedback may be provided to avoid a collision while modifying the bone for other implant components/features (e.g., projecting a section view (or other view) of the keel model 150, or projecting a section view (or other view) of an entire implant itself). It should be further appreciated that other pre-operative bone data or implant data may be used in lieu of 3-D models to provide the visual feedback. For example, the 3-D bone models may be a series of 2-D views of the bones, the raw imaging data of the bones (e.g., Digital Imaging and Communications in Medicine (DICOM) data), generic virtual bone models, and other types of pre-operative bone data as described above. Likewise, the implant model may be any other representation of the implant illustratively including one or more 2-D images of the implant, a triangular mesh of the implant, a point cloud of the implant, etc.

After the user has positioned the femur "F" and/or tibia "T", or decided to skip one or more cuts to be made on the bones with the surgical robot 132, the remainder of the TKA procedure is executed to modify the femur "F" and tibia "T" to receive the implants according to the surgical plan. If the user decided to skip one or more cuts, the skipped cuts may be completed using manual instrumentation or other techniques. The final implants are then installed on the bone and the TKA procedure is complete.

Figure 11:
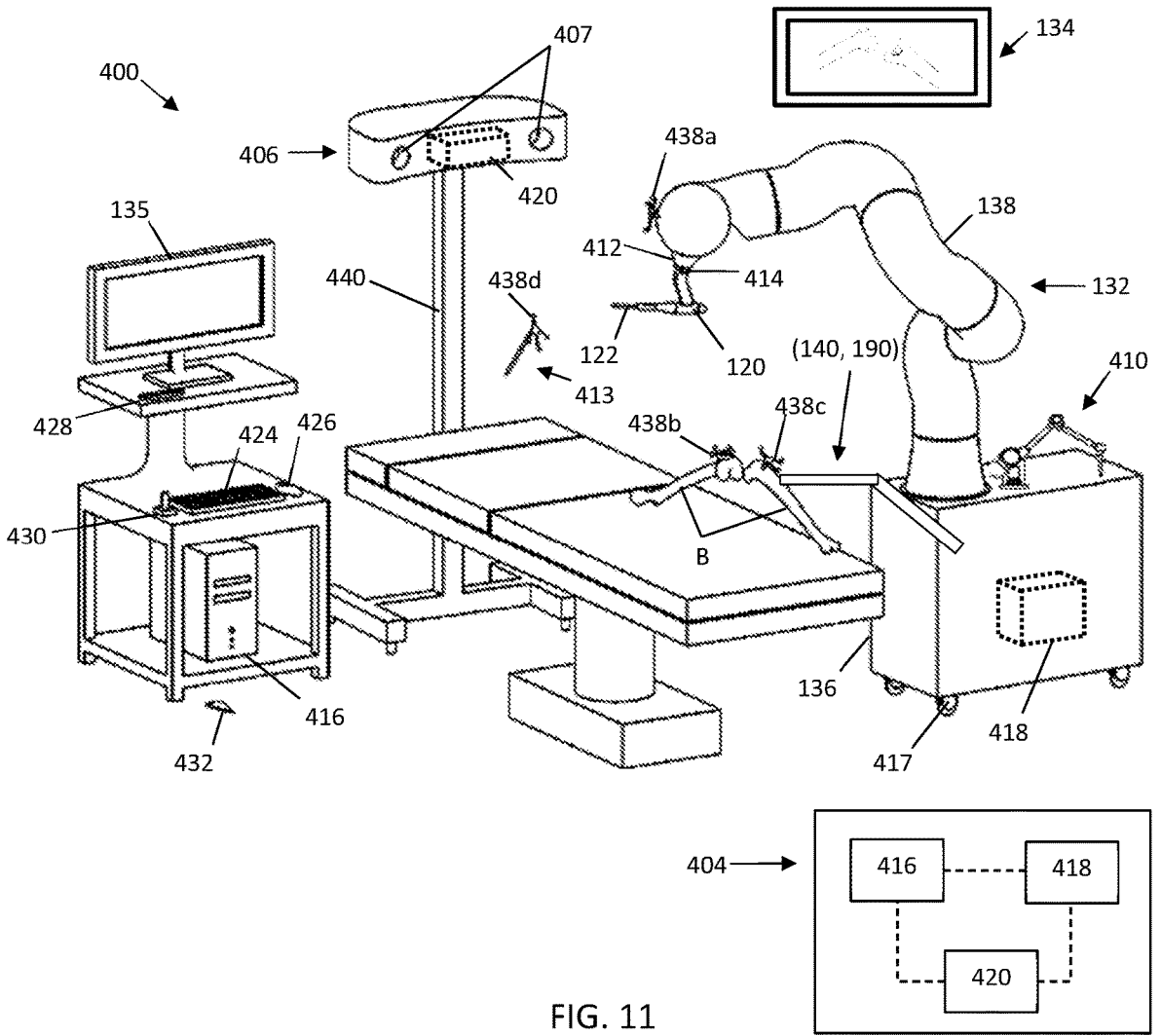
FIG. 11 depicts a robotic surgical system for executing a joint replacement procedure and to assist in positioning the bones in the OR prior to the procedure.

In a particular embodiment, the surgical robot 132 does not include fixator arms 140 but instead uses a tracking system (e.g., an optical tracking system as denoted at 406 in FIG. 11). An example of an optical tracking system operative herein is found in U.S. Pat. No. 6,061,644 and further detailed with respect to FIG. 11. After the bone is exposed in a traditional manner, a tracking element (e.g., tracking arrays as denoted as 438b and 438c in FIG. 11) is affixed to each bone. The surgical plan is then registered to each bone relative to the coordinate frame of the tracking element to permit the tracking system to track the POSE of the surgical plan as the bones move in the OR. After registration, the same procedure to provide visual feedback to the user may implemented. For example, a femur bone model 'FM' and tibia bone model 'TM' are displayed on the monitor 134 that reflects the actual position of the femur "F" and tibia "T" relative to one another in the OR. The displayed position of the femur bone model 'FM' and tibia bone model 'TM' may be updated in real-time as the femur "F" and tibia "T" move in the OR, by way of the 3-D bone models being registered to the bones relative to the coordinate frame of the tracking elements affixed to the bones, and the tracking elements being tracked by the tracking system. A section view of a feature or component of the implant, for example, post model 148, may be projected normal to its cutting axis and through the opposing bone model, as described above. The location of the projection of the section view 152 may likewise be updated in real-time as the femur "F" or tibia "T" move in the OR by updating/calculating, in real-time, the transformation between: a) the coordinates of the section view 152 in the coordinate frame of the registered tibial bone model 'TM'; and b) the coordinate frame of the registered femoral bone model 'FM'. Alternatively, the section view 152 may be projected beyond the tibial bone model 'TM' a sufficient distance to possibly intersect with the femur bone model 'FM' as previously described. Therefore, a user, in may adjust the position of either bone to avoid a collision during the procedure, even while the surgical robot 132 is actively modifying a bone, and even in real-time.

In particular embodiments, the computer software internally computes if there is a potential collision of the end-effector 120 with bystander anatomy and provides feedback to the user (e.g., a visual alert, an audible alert, tactile sensation). After the bone models are registered to their respective bone models, the computer determines if the end-effector 120 will collide with the bystander anatomy using: i) a registered position of a bone model to bystander anatomy; and ii) a registered orientation of an end-effector axis 125 (as shown in FIG. 2) that the end-effector 120 will assume while modifying parts of a bone opposing the bystander anatomy. The end-effector axis 125 may represent a longitudinal axis of the tool 122 or a longitudinal axis of a sleeve 124 of the end-effector 120 as shown in FIG. 1B. In a particular example for determining a potential collision, a femoral bone model 'FM' is registered to the femur 'F' and a cut-file is registered to the tibia 'T'. If a cut-file is positioned with respect to a tibia bone model 'TM' during the planning phase, then registration of a tibia bone model 'TM' also registers the cut-file to the planned location on the bone in order to direct the end-effector 120 to create the bone cuts according to the planned position for an implant. The computer then knows or can calculate the position and orientation of the femur 'F' based on the position of the registered femoral bone model 'FM'. The cut-file includes the orientations (or vectors) that the end-effector axis 125 will assume while forming the post hole 110 or keel hole 112 in the tibia 'T' and since the cut-file is registered to the tibia 'T', the computer knows or can calculate the orientations that the end-effector axis 125 will assume when forming the post hole 148 or keel hole 150 in the tibia 'T'. The computer may then determine a potential collision by calculating if any orientations of the end-effector axis 125 (as defined in the registered cut-file) spatially overlaps (e.g., intersects, contacts) the registered femoral bone model 'FM; (and therefore the actual femur 'F') while forming the post hole 110 or keel hole 112 in the tibia 'T'. This is determined using: i) the known POSE of the femur 'F' according to the position of the registered femoral bone model 'FM'; and ii) the known orientations that the end-effector axis 125 will assume while forming the post hole 148 or keel hole 150 in the tibia 'T' according to the orientations defined in the cut-file registered to the tibia 'T'. The computer may further use the geometry of the end-effector 120 along the end-effector axis 125 (e.g., the diameter of the sleeve 124 (as shown in FIG. 1B), the diameter of an end-mill, drill bit, etc.) in the determination. For instance, the computer may model the end-effector 120 along the end-effector axis 125 as a cylinder having the same diameter as the sleeve 124. The computer then determines if any part of the cylinder collides with the registered femoral bone model 'FM' at any of the end-effector axis orientations defined in the cut-file. If the computer determines a collision will occur, the computer may provide feedback (e.g., a visual alarm, audible alarm, tactile feedback) and may indicate that the end-effector may collide with bystander anatomy. The computer may also present the user with options including at least one of: a) reposition the bone and/or bystander anatomy; or b) limit the number of the one or more cuts to be created on the first bone with the CAS device.

In another embodiment, the computer software may internally compute if there is a potential collision of the end-effector 120 with bystander anatomy using: i) the registered position of the bone models to the bones; and ii) one or more features (e.g., post model 148) of an implant model registered to the bone. Instead of using the known orientations of the end-effector axis as defined in a cut-file as previously described, one or more axes or cross-section of a feature of an implant model may be used, which corresponds to the orientation of that the end-effector axis will assume while modifying a part of the bone. For example, a femoral bone model 'FM' and tibial implant model 146 are first registered to their respective bones. If a tibial implant model 146 is positioned with respect to a tibia bone model 'TM' during the planning phase, then registering a tibial bone model 'TM' to the tibia 'T' also registers the tibial implant model 146 to the planned location on the tibia 'T'. Based on the registered position of the tibia implant model 146, the computer knows or can determine a POSE of at least one of a longitudinal axis of the post model 148, an axis normal to a cross-section of the post model 148, or a projection of a cross-section of the post model 148, all of which will represent at least one orientation that the end-effector axis 125 will assume while forming the post hole 110 in the tibia 'T'. A plurality of longitudinal axes of the post 148 or axes normal to a cross-section of the post 148 may be determined to represent or to account for a plurality of end-effector axis orientations that the end-effector 120 will assume to form the post hole 110 in the tibia 'T'. The computer may then determine a potential collision between the end-effector 120 and the femur 'F' while modifying the tibia 'T' by calculating any spatial overlap between the registered femoral bone model 'FM' and at least one of the following: a) an axis (or axes) of a longitudinal axis of the post model 148 registered to the tibia 'T'; b) an axis (or axes) normal to a cross-section of the post model 148 registered to the tibia 'T'; or c) a projection of a cross-section of the post model 148 registered to the tibia 'T'. The computer may further use the geometry of the end-effector 120 along the end-effector axis 125 (e.g., the diameter of the sleeve 124 (as shown in FIG. 1B), the diameter of an end-mill, drill bit, etc.) in the determination by applying the geometry about the axis (or axes) of the post model 148. If the computer determines a collision will occur, the computer may provide feedback (e.g., a visual alarm, audible alarm, tactile feedback) and may indicate that the end-effector 120 may collide with bystander anatomy. The computer may also present the user with options including at least one of: a) reposition the bone and/or bystander anatomy; or b) limit the number of the one or more cuts to be created on the first bone with the CAS device.

Feedback to Position Bones with Pre-Operative and Intra-Operative Data

Figure 4:
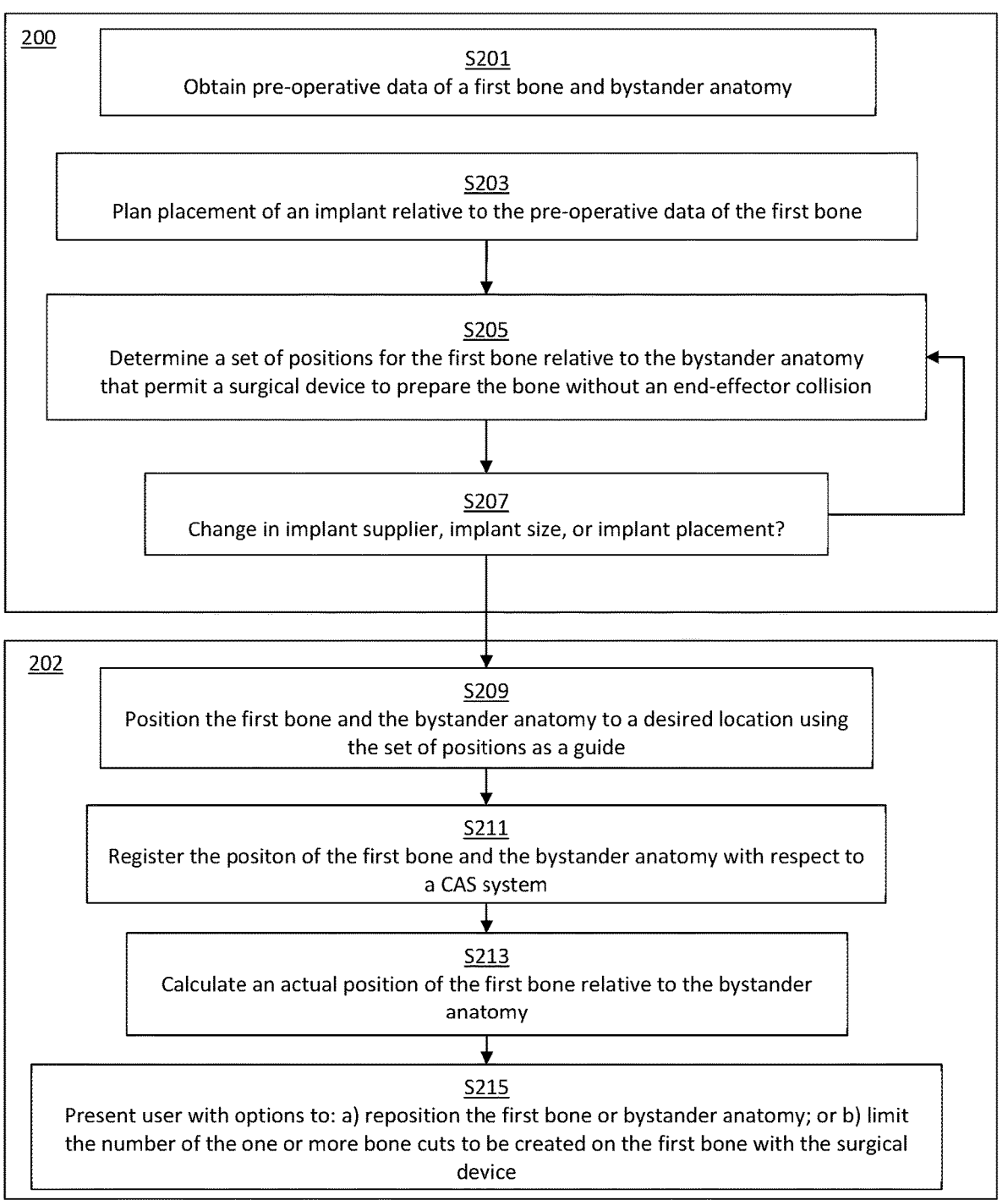
FIG. 4 illustrates a method to provide pre-operative and intra-operative feedback to a user to assist in positioning the bones in the OR prior to a joint replacement procedure.
Figure 5:
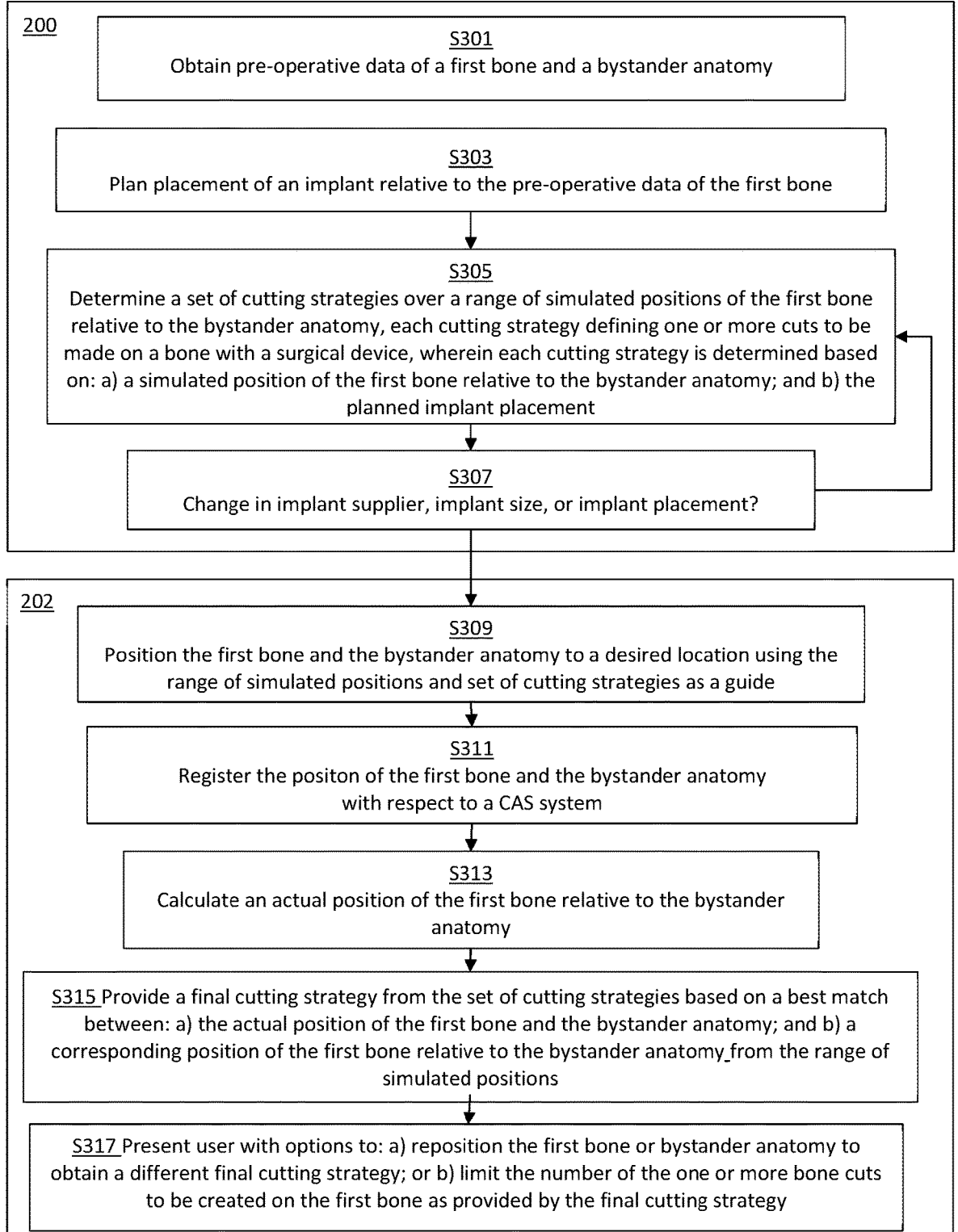
FIG. 5 illustrates another method to provide pre-operative and intra-operative feedback to a user to assist in positioning the bones in the OR prior to a joint replacement procedure.

With reference to FIGS. 4, 5, and 6A-6C, a specific embodiment for providing feedback to assist a user in positioning bones is shown that utilizes both pre-operative and intra-operative feedback. With reference first to FIG. 4, a method to assist a user in positioning the bones may begin pre-operatively (pre-operative operations are designated in block 200) with pre-operative planning software. It is appreciated that like data is obtained in different ways without departing from the collision avoidance of the present invention. Pre-operative bone data of a first bone and a second bone is generated or obtained [S201]. A user plans the placement of one or more implants relative to the pre-operative bone of the first bone and/or second bone [S203]. A set of positions for the first bone relative to the second bone are determined that will permit a CAS device to prepare the bone without an end-effector collision [S205]. If the user selects a different implant supplier catalog, size, or changes the placement of the implant relative to the pre-operative bone data [S207], then a new set of positions are determined as in the previous step [S205]. Intra-operatively (intra-operative operations are designated in block 202), the first bone and second bone are positioned relative to one another and may be positioned in a desired location using the pre-operatively determined set of positions as a guide [S209]. After the bones are positioned (e.g., fixed in position), the surgical plan is registered to each bone with respect to a CAS system [S211]. The actual position of the first bone relative to the second bone is then calculated using the registered position of the bones [S213]. Based on the calculated position of the bones, the user may be presented with options for end-effector collision avoidance with bystander anatomy. The options may be include: a) reposition the first bone and/or bystander anatomy; or b) limit the number of the one or more cuts to be created on the first bone with the CAS device in a given orientation [S215]; or c) alternate between cuts on the faces of the opposing bones. Particular embodiments of the method will now be described.

Pre-operative bone data of the first bone and bystander anatomy, such as a second bone of the joint, may be obtained or generated [S201] by a variety of means. In a particular embodiment, pre-operative images of the bones are obtained using an imaging modality (e.g., CT, MRI, etc.). The pre-operative images are loaded into pre-operative planning software and processed to segment the bones from the surrounding tissues, where the segmented bones are used to build a 3-D models of each bone using techniques known in the art (e.g., marching cubes).

A user may then plan the placement of one or more implants relative to the pre-operative bone data [S203]. Pre-operative planning software running on a computer may include a GUI, an implant library, and various tools or widgets to assist in planning. The implant library may include a plurality of implant supplier catalogs (e.g., implants from different manufacturers), implant sizes, and implant types (femoral implants vs. tibial implants) in the form of 3-D implant CAD models. The user may select and re-select different implants and place the implants relative to the pre-operative bone data to designate the best fit, fill, or alignment for the final implants on the bones.

Once the user identifies a candidate implant and POSE for the implant relative to the pre-operative bone data, the pre-operative planning software may determine or calculate a set of positions (e.g., the joint angle and subluxation) for the first bone relative to the second bone that will permit a CAS device to create one or more cuts on the first bone and/or second bone to receive the implant in the planned placement [S205]. The set of positions reflect one or more positions for the first bone relative to the second bone that will not cause an end-effector collision with the opposing bone. The set of positions may be determined or calculated by simulating the cutting process for different positions of the bones as described in U.S. Patent App. Pub. US20200405394A1 assigned to the assignee of the present application and incorporated by reference herein. In short, the bones are iteratively positioned in different POSEs relative to one another, and for each iteration an end-effector model is used to simulate the cut on the bones to receive the implants as planned. Any iteration (i.e., a particular position of one bone relative to the other) that does not result in any part/portion of the end-effector model colliding with the opposing bone model is included in the set of positions in step [S205]. The set of determined positions may then be provided to the user in the GUI (e.g., in a text table, graph, graphics, illustrations, simulations, or other form). The set of positions may include the joint angles (e.g., the angle between the femur "F" and tibia "T") and subluxations (e.g., a distance measurement between the femur "F" and tibia "T") that will avoid an end-effector collision with the opposing bone or bystander anatomy. If at any point the user changes the implant line, type, size, or position of the implants [S207], then step [S205] is repeated to determine a new set of positions for that particular implant line, type, size, and/or position that will avoid an end-effector collision.

In the OR, the patient is prepped in a typical manner and the bones are exposed. The user then positions the two bones relative to one another [S209] and may fix the bones to the CAS device or affix a tracking element to each bone. The user may position the bones with the aid of the set of positions determined pre-operatively in step [S205]. A monitor in the OR may display the set of joint angles and subluxations that will avoid an end-effector collision. The user may use the suggested joint angles and subluxations as a guide to roughly position the bones.

After the bones are fixed or trackable relative to the CAS system, the surgical plan is registered to the bones [S211] using registration techniques known in the art. Then using the registered position of the bones, the actual position of the first bone relative to the second bone is calculated [S213]. For example, the joint angles and subluxation between the first bone and second bone may be calculated based on the registered positions of the 3-D bone models to the bones. The 3-D bone models are mapped onto the position of the bones through the registration process, which allows for the calculations to be made using the registered position of the 3-D bone models. Anatomical landmarks, or designated points, lines, or planes on or associated with the 3-D bone models may provide the reference features for calculating the joint angle and subluxation. For example, the joint angle may be calculated as the angle between: a) an axial plane on the most distal portion of the femur bone model 'FM'; and b) a plane representing the tibial plateau of the tibial bone model 'TM'. The subluxation may be calculated as the distance between: a) a most distal point on the medial condyle of the femur bone model 'FM'; and b) the most proximal point of the medial intercondylar tubercle of the tibial bone model 'TM'. It should be appreciated that any anatomical landmark, or other designated point, line, or plane may be used as long as those anatomical landmarks, points, lines, or planes remain consistent between the pre-operative and intra-operative calculations.

Once the actual position of the first bone relative to the second bone is known, the actual position is compared to the set of positions determined preoperatively in step [S205] to determine if an end-effector collision might occur. For example, the actual position of the bones may match with a position of the bone models in the set of positions as determined in step [S205], which concludes that an end-effector collision is unlikely to occur. On the contrary, if the actual position of the bones does not match to at least one position in the determined set of positions in step then an end-effector collision may occur. The GUI may display a signal indicating that the bones are indeed positioned in a manner that will avoid an end-effector collision. For example, the signal may be a green light, auditory, text, or other signal. Alternatively, the GUI may display a signal indicating that the bones are positioned in a manner that may cause an end-effector collision. In this instance, the user may presented with options. The options may include: a) reposition the first bone and/or second bone; or b) limit the number of the one or more bone cuts to be created on the first bone and/or second bone [S215]. The first option allows the user to reposition the bones in a better position that will more likely avoid an end-effector collision. The second option may pull up a drop down menu or otherwise provide the user with additional options to choose which cuts to limit (i.e., cuts to skip). For example, the user may have the option to skip the cutting of the post hole 110 or keel hole 112 if those cuts are deemed likely to cause an end-effector collision. Therefore, if those cuts are skipped then the risk of an end-effector collision is mitigated. The CAS device may then prepare the other portions (non-skipped portions) of the bone, and the skipped cuts may be completed with manual instrumentation. Finally, the implants are placed on the bones and the surgery is complete.

With reference now to FIGS. 5, and 6A-6C, a specific embodiment of a method for providing feedback to assist a user in positioning bones is shown that also utilizes both pre-operative and intra-operative feedback. The method may begin pre-operatively (pre-operative operations are designated in block 200) with pre-operative planning software. Pre-operative bone data of a first bone and a second bone is generated or obtained [S301]. A user plans the placement of one or more implants relative to the pre-operative bone of the first bone and/or second bone [S303]. A set of cutting strategies is determined over a range of simulated bone positions, where each cutting strategy defines one or more cuts to be made on a bone with a CAS device. Each cutting strategy may be determined based on: a) a simulated position of the first bone relative to the second bone; and b) the planned implant placement relative to the pre-operative bone data [S305]. If the user selects a different implant line, size, or changes the placement of the implant relative to the pre-operative bone data [S307], then a new set of positions are determined as in the previous step [S305]. Intra-operatively (intra-operative operations are designated in block 202), the first bone and second bone are positioned relative to one another and may be positioned in a desired location using the range of simulated positions and set of cutting strategies (as determined preoperatively) as a guide [S309]. After the bones are positioned (e.g., fixed in position), the surgical plan is registered to each bone with respect to a CAS system [S311]. The actual position of the first bone relative to the second bone is then calculated using the registered position of the bones [S313]. A final cutting strategy from the set of cutting strategies is provided to the user based on a best match between: a) the actual position of the bones; and b) a corresponding position of the bones in the range of simulated positions [S315]. The user may also be presented with options to avoid an end-effector collision. The options may be include: a) reposition the first bone and/or second bone; or b) limit the number of the one or more cuts to be created on the first bone and/or second bone with the CAS device [S317]. Particular embodiments of the method will now be described.

Obtaining or generating the pre-operative bone data [S301] and planning the placement of an implant [S303] may be performed in the same manner as described with reference to FIG. 4. Once the user identifies a candidate implant and POSE for the implant relative to the pre-operative bone data, the pre-operative planning software may determine or calculate a set of cutting strategies over a range of simulated bone positions, where each cutting strategy defines one or more cuts to be made on a bone with a CAS device, and where each cutting strategy is determined based on: a) a simulated positions of the first bone relative to the second bone; and b) the planned placement of the implant [S305]. The set of cutting strategies may be determined or calculated by simulating the cutting process for different positions of the bones as described in U.S. Patent App. Pub. US20200405394A1 assigned to the assignee of the present application and incorporated by reference herein. Here, the bones are iteratively positioned in different POSEs relative to one another, and for each iteration an end-effector model is used to simulate the cut on the bones to receive the implants as planned. For each iteration (i.e., a particular position of one bone relative to the other) the planning software records if an end-effector collision occurred or not. If an end-effector collision did occur during a simulation, the software records which implant feature/portion was being cut in the bone (e.g., post hole) when the collision occurred. This process is repeated over a range of simulated bone positions. For each simulated bone position (e.g., a specific joint angle and subluxation), a cutting strategy is determined that provides the user with what implant features/portions may or may not be cut on the bone to avoid an end-effector collision. The set of cutting strategies and bone positions may then be provided to the user in the GUI (e.g., in a text table, graph, graphics, illustrations, simulations, or other form). For example, with reference to FIG. 6A, a monitor 135 associated with the pre-operative planning software may display a table 160. Each simulated bone position (e.g., joint angle and subluxation) is shown in each row with a corresponding cutting strategy. The range of simulated bone positions is represented by rows 1:N. The cutting strategies refer to which cuts may or may not be made on the bone to avoid an end-effector collision. For example, in row 1, the simulated position between the first bone and the second bone is a joint angle of 20 degrees and subluxation of 5 cm. At this bone position, the simulations determined that an end-effector collision would occur while cutting the post hole 110 and the keel hole 112. Therefore, the user is presented with a cutting strategy to avoid cutting the post hole 110 and keel hole 112 with the CAS device with end-effector collision avoidance. In another example, row 2 shows that a joint angle of 20 degrees and a subluxation of 10 cm between the first bone and second bone allows for the cutting of the post hole 110 and keel marks, but not the entire keel hole 112. Keel marks refer to one or more reference holes, divots, imprints, or other features that the CAS device may create on the bone, where the keel marks assist the user in aligning a manual instrument to create the keel holes 112. In a final example, row 6 shows that a joint angle of 40 degrees and subluxation of 10 cm between the first bone and second bone allows for the cutting of the post hole 110 and the keel holes 112 without an end-effector collision. If at any point the user changes the implant line, type, size, or position of the implants [S307], then step [S305] is repeated to determine a new set of cutting strategies for that particular implant line, type, size, and/or position that will avoid an end-effector collision.

In the OR, the patient is prepped in a typical manner and the bones are exposed. The user then positions the two bones relative to one another [S309] and may fix the bones to the CAS device or affix a tracking element to each bone. The user may position the bones with the aid of the set of positions and cutting strategies determined pre-operatively in step [S305]. A monitor 134 in the OR may display the set of joint angles, subluxations, and cutting strategies. The user may use the suggested joint angles and subluxations as a guide to roughly position the bones to achieve the desired cutting strategy. For example, in reference FIG. 6B, a monitor 134 in the OR may display the same table 160 as was presented pre-operatively. The user may attempt to position the bones with a joint angle of 40 degrees and a subluxation of 10 cm to ensure the CAS device can prepare the post hole 110 and keel 112 without an end-effector collision.

After the bones are positioned and fixed or trackable relative to the CAS system, the surgical plan is registered to the bones [S311] using registration techniques known in the art. Then using the registered position of the bones, the actual position of the first bone relative to the second bone is calculated [S313]. For example, the joint angles and subluxation between the first bone and second bone may be calculated based on the registered positions of the 3-D bone models to the bones as described above.

Once the actual position of the bones are calculated, a final cutting strategy from the set of cutting strategies is provided to the user. The final cutting strategy is determined based on a best match between: a) the actual position of the first bone relative to the second bone; and b) a corresponding position of the first bone relative to the second bone from the range of simulated bone positions [S315]. For example, with reference to 6C, the monitor 134 in the OR may display the actual position of the bones and the resulting final cutting strategy. The CAS system may have determined that the actual position of the bones in the OR is a joint angle of 30 degrees and subluxation of 10 cm. This corresponds to the simulated bone position in row 4 of table 160, which results in a final cutting strategy that permits the CAS device to create the post hole 110 and keel marks. The user was slightly off when initially positioning the bones in the OR (i.e., they did not achieve a joint angle of 40 degrees and subluxation of 10 cm). In this instance, the monitor 134 may display options for the user. The options may include: a) reposition the first bone and/or second bone; b) limit the number of the one or more bone cuts to be created on the first bone and/or second bone [S317]; or c) alternate between cuts on the faces of the opposing bones. The first option allows the user to reposition the bones in a better position that will more likely avoid an end-effector collision and/or to permit the CAS device to create the feature in the bone. The second option may pull up a drop down menu or otherwise provide the user with additional options to choose which cuts to limit (i.e., cuts to skip). For example, the user may now have the option to skip the cutting of the keel hole 112 to avoid an end-effector collision. The CAS device may then prepare the other portions (non-skipped portions) of the bone, and the skipped cuts may be completed with manual instrumentation. Finally, the implants are placed on the bones and the surgery is complete.

Bone Positioning with Alignment Devices or Measuring Devices

Figure 7:
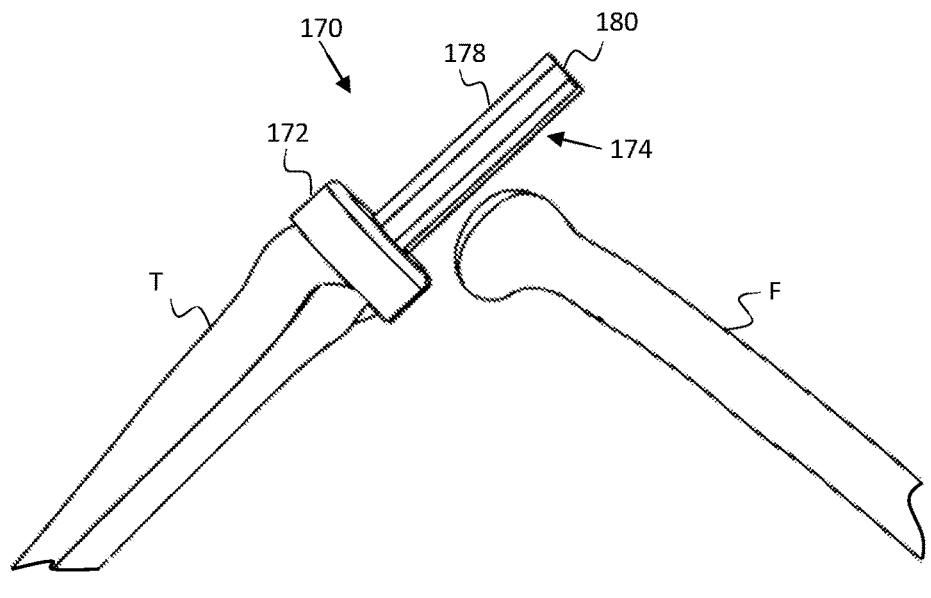
FIG. 7 depicts a tibia, a femur, and an alignment device to assess a potential end-effector collision.

With reference to FIGS. 7, 8A-8C, and 9, a specific embodiment for assisting a user in positioning bones is shown that utilizes one or more alignment devices. In a particular embodiment, with reference to FIGS. 7 and 8A, a first alignment device 170 is shown. The alignment device 170 includes a base 172, and an alignment feature 174 projecting from the base 172. The base 172 may be shaped to represent the nominal shape of a bone, for example, the proximal tibial bone shape in its natural form. The alignment feature 174 may be sized and shaped to represent the path of the end-effector. The alignment device 170 is configured to be placed upon the bone for example, the tibial plateau as shown in FIG. 7, prior to cutting to show the path or orientation of the end-effector and therefore whether the end-effector might collide with the opposing bone. For example, in FIG. 7, when the alignment device 170 is placed on the tibia "T", the alignment feature 174 (which represents the path of the end-effector) does not collide with the femur "F", and therefore it is unlikely that the end-effector will collide with the femur "F" while preparing the tibia "T".

Figures 8A, 8B, 8C:
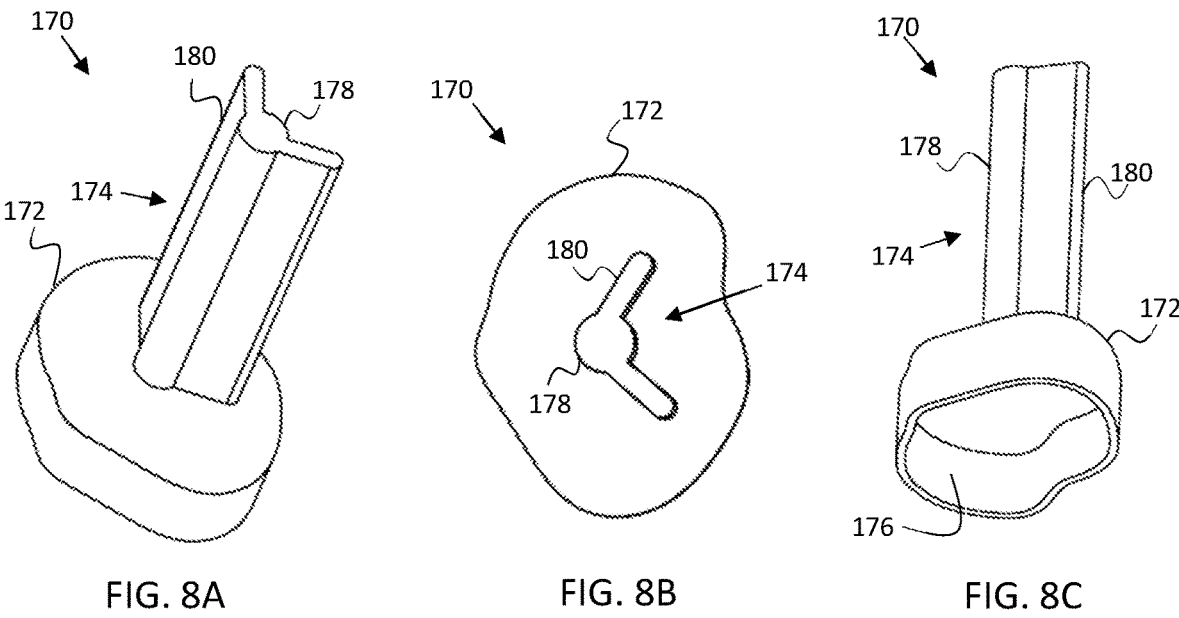
FIGS. 8A-8C depict a particular alignment device for placement on a tibia to assess a potential end-effector collision with the femur, where

With reference to FIGS. 8A-8C, a particular embodiment of the alignment device 170 is shown. The base 172 has the nominal shape of the proximal tibia "T" and may fit over a portion of the proximal tibia "T". For example, the base 172 may have a shelled interior 176 to receive the proximal tibia "T" therein. The alignment feature 174 represent the path of the end-effector and may have the size and shape of one or more implant features/components to be cut in the bone. For example, the alignment feature 174 may include a post hole feature 178 and a keel hole feature 180 projecting from the base. The post hole feature 178 and keel hole feature 180 may project from the base 172 by a suitable length to intersect with the femur "F" to assess the potential for an end-effector collision. Furthermore, the alignment feature 174 may be sized with an additional margin of thickness or width to ensure there is enough clearance for the end-effector during the surgery. If the alignment device 170 when placed upon the proximal tibia "T" prior to cutting shows that there is not enough clearance between the alignment feature 174 and the opposing bone, then the bones should be re-positioned prior to registration. This is one primary advantage of using the alignment device 170 because a user may assess whether an end-effector collision may occur before registering the bones.

It should be appreciated that other shapes and sizes for the alignment device 170, base 172, and alignment feature 174 may be designed. For example, the base 172 may be adapted to fit on a distal end of the femur "F", where the alignment feature 174 is one or more peg hole features extending from the base 172. The peg hole features represent the pegs of a femoral TKA implant. When placing the alignment device 170 on the distal femur, a user can identify if an end-effector collision might occur with the tibia "T" as the end-effector prepares the peg holes to receive the pegs of the femoral TKA implant. The same applies to any other bone, implant, or implant features to assess a potential end-effector collision.

Figure 9:
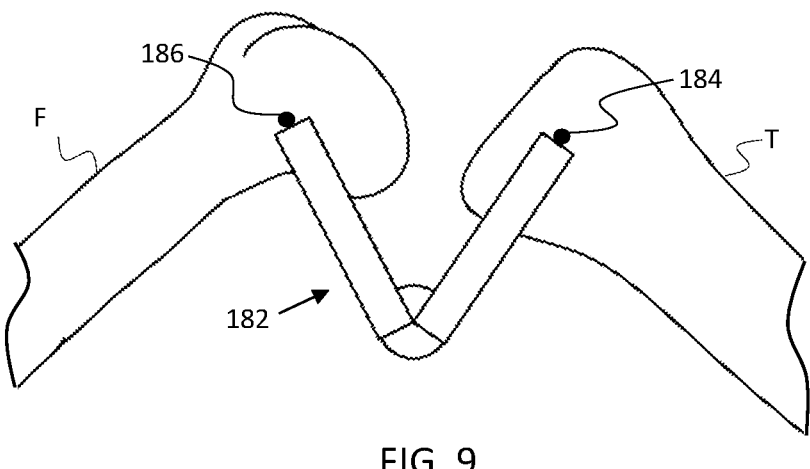
FIG. 9 depicts a femur, a tibia, and a measurement device to assist in positioning the bones in the OR prior to a joint replacement procedure.

With reference to FIG. 9, another embodiment for providing feedback to assist a user in positioning bones is shown that utilizes a measuring device 182. A measuring device 182 (e.g., goniometer, protractor, compass, ruler) may be used to measure the angle and a distance from a tibial landmark 184 and a femoral landmark 186 to determine if any positioning requirements are satisfied. For example, a goniometer may be used to measure the joint angle between the femur "F" and tibia "T" using the lateral epicondyle of the femur "F" and the lateral condyle of the tibia "T". It should be appreciated that numerous anatomical landmarks exist to permit such measurements. The use of the measuring device 182 may be combined with the methods described in FIGS. 4 and 5. For example, at step [S209] or [S309] the measuring device 182 may be used to measure and obtain a desired joint angle and subluxation as suggested by the results of step [S205] or [S305].

Bone Positioning with Fixation Elements

Figure 10:
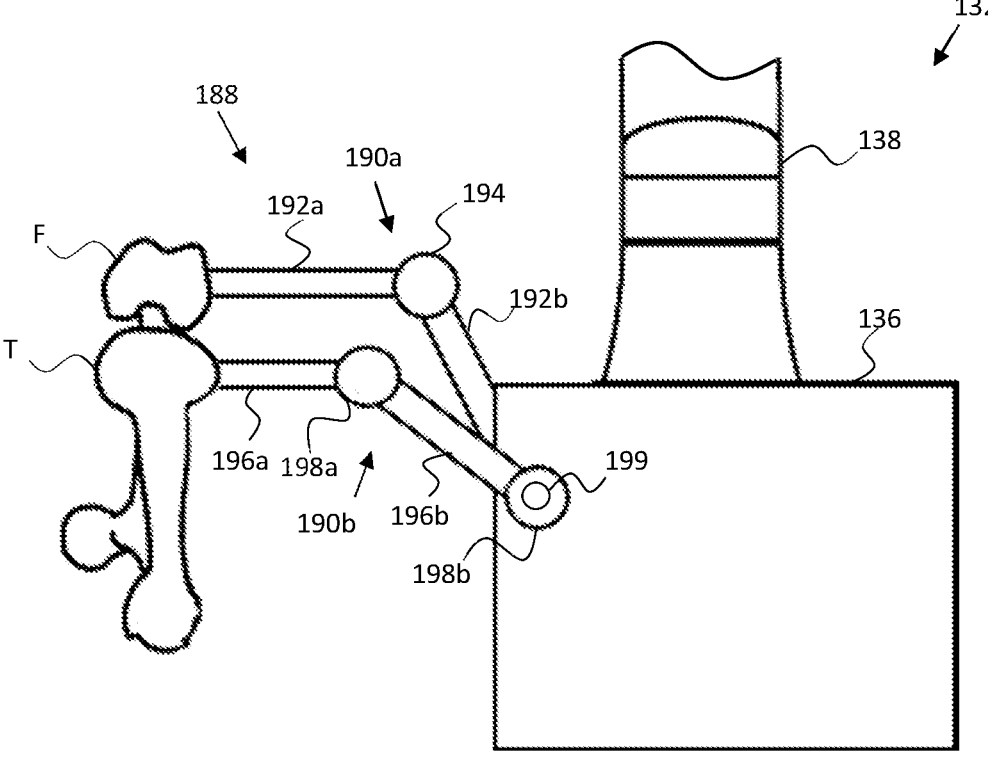
FIG. 10 depicts a fixation system to fix the bones in a desired position in the OR prior to a joint replacement procedure.

With reference to FIG. 10, a specific embodiment for assisting a user in positioning bones is shown that utilizes a fixation system. The fixation system and a method of its use provides a way to ensure surgical success during cutting by limiting the joint fixation to positions that are viable during use of a CAS device (e.g., surgical robot). If the patient cannot be put into the correct position, then the fixation system cannot lock into place. The fixation system may include fixation elements that attach to the patient and position the bones at a desired location (e.g., joint angle and subluxation), providing the clearance, and in some case an additional margin of clearance, required for most surgical plans. Additionally, the fixation system can be set for different cutting strategies. For example, the fixation system may provide the user with different options, where the fixation elements lock in place to position the bones at different locations to allow of full operative cutting or partial operative cutting. For a tibia "T", full operative cutting allows for the creation of the tibial plateau 108, post hole 110, and keel holes 112, while partial operative cutting may skip certain cuts and only allow for the cutting of: a) the tibial plateau 108; b) the tibial plateau 108 and post hole 110; or c) the tibial plateau 108, post hole 110, and keel marks.

In a particular embodiment, the fixation system 188 includes a first fixation arm 190a and a second fixation arm 190b. The fixation arms (190a, 190b) may be positioned on opposing sides of a surgical robot 132, and may be more particularly positioned on opposing sides of the base 136 of a surgical robot 132. The first fixation arm 190a may include a plurality of links (192a, 192b) joined together by one or more joints 194. Likewise, the second fixation arm 190b may also include a plurality of links (196a, 196b) joined together by one or more joints (198a, 198b). A distal end of the most distal links (192a, 196a) further includes an attachment mechanism (e.g., clamp, screw, pin) to securely fix the fixation arms (190a, 190b) to the bones. The joints (194, and 198a, 198b) permit the links (192a, 192b and 196a, 196b) to translate or rotate relative to one another, while further having one or more locking mechanisms (e.g., a ratcheting lock, a clamping lock) to lock the links (192a, 192b, or 196a, 196b) in a set or desired position. For example, the joints (194, 198a, 198b) may be locking ball joints, locking rotary joints, or locking prismatic joints. The joints (194, 198a, 198b) may further include encoders or other measuring device to determine the relative translational or rotational position of the links (192a, 192b, or 196a, 196b) to one another. Each joint (194, 198a, 198b) also includes a dial 199 (digital or manual), or other user input mechanism, for the user to designate the locking position for the joints (194, 198a, 198b), and therefore the position in which the bones need to be placed for the fixation system 188 to lock in place. For example, a user may set the dial(s) 199 to have the fixation arms (190a, 190b) only lock in place when the bones are positioned in a location that achieves a desired joint angle and subluxation. A user may set the dial(s) 199 according to the feedback described in the methods of FIGS. 4 and 5. That is, at step [S209] or [S309], the user may set the dial(s) 199 to obtain a desired joint angle and subluxation based on the results from step [S205] or [S305].

The fixation system 188 may be used in the following manner. A user affixes the first fixation arm 190a to the femur "F" and the second fixation arm 190b to the tibia "T". The fixation arms (190a, 190b) may affixed to the bones by way of a clamp on the distal links (192a, 192b) being clamped onto one or more pins or screws that were inserted into the femur "F" and tibia "T". The user may then set the dial(s) 199 to achieve a desired joint angle and subluxation. The user may use the feedback from steps [S205] and [S305] in the methods of FIGS. 4 and 5 as a guide for setting the dial(s) 199. After which, the user maneuvers the bones until the joints (194, 198a, 198b) lock into position, therefore ensuring the bones are at a desired joint angle and subluxation. The remainder of the procedure may proceed in a typical manner. It should be appreciated that other intraoperative steps as described in the methods of FIGS. 4 and 5 may be executed at this time to ensure the bones are in the desired POSE and/or to select a desired cutting strategy.

Robotic Surgical System

FIG. 11 depicts a particular embodiment of a CAS system in the form of a robotic surgical system 400. The robotic surgical system 400 is shown in the context of an operating room (OR) to prepare a femoral and tibial bone for total knee arthroplasty. The surgical system 400 includes a surgical robot 132, a computing system 404, and an optional tracking system 406. The surgical robot 132 may include a movable base 136, a robot arm 138 connected to the base 136, an end-effector 120 located at a distal end 412 of the robot arm 138, and a force sensor 414 positioned proximal to the end-effector 120 for sensing forces experienced on the end-effector 120. The base 136 includes a set of wheels 417 to maneuver the base 136, which may be fixed into position using a braking mechanism such as a hydraulic brake. The base 136 may further include an actuator to adjust the height of the robot arm 138. The robot arm 138 includes various joints, links, and sensors (e.g., encoders) to accurately manipulate the end-effector 120 in various degrees of freedom. The joints are illustratively prismatic, revolute, spherical, or a combination thereof. The end-effector 120 may be a motor-driven end-mill, cutter, drill-bit, or other bone removal device. In some embodiments, the surgical system 400 further includes a mechanical digitizer arm 410 attached to the base 136 to assist in digitizing the bones and/or the registration process. In other inventive embodiments, the system includes a tracked hand-held digitizer device 413 with a probe tip to be tracked by the tracking system 406, where hand-held digitizer device 413 assists in digitizing the bones and/or the registration process.

The computing system 404 may generally include a planning computer 416; a device computer 418; a tracking computer 420 (if present); and peripheral devices. The planning computer 416, device computer 418, and tracking computer 420 may be separate entities, one-in-the-same, or combinations thereof depending on the surgical system. Further, in some embodiments, a combination of the planning computer 416, the device computer 418, and/or tracking computer 420 are connected via a wired or wireless communication. The peripheral devices allow a user to interface with the surgical system components (intraoperatively and/or preoperatively) and may include: one or more user-interfaces, such as a display or monitor (134, 135) to display a graphical user interface (GUI); and user-input mechanisms, such as a keyboard 424, mouse 426, pendent 428, joystick 430, foot pedal 432, or the monitor (134, 135) in some inventive embodiments has touchscreen capabilities.

The planning computer 416 contains hardware (e.g., processors, controllers, and/or memory), software, data and utilities that are in some inventive embodiments dedicated to the planning of a surgical procedure, either pre-operatively or intra-operatively. This may include reading pre-operative bone data, displaying pre-operative bone data, manipulating pre-operative bone data (e.g., image segmentation), constructing three-dimensional (3D) virtual models, storing computer-aided design (CAD) files, providing various tools, functions, or widgets to aid a user in planning the surgical procedure, and generating surgical plan data. The final surgical plan may include: pre-operative bone data (e.g., 3-D virtual bone models); patient identifier data; registration data including the position of a set of points P defined relative to the pre-operative bone data for registration; virtual implant models positioned relative to the pre-operative bone data; and/or a set of instructions to operate the surgical robot 138. The set of instructions may include instructions for the surgical robot 138 to modify a volume of bone to receive an implant. The set of instructions may illustratively be: a cut-file having a set of cutting parameters/instructions (e.g., cut paths, velocities) to automatically modify the volume of bone; a set of virtual boundaries defined to haptically constrain a tool within the defined boundaries to modify the bone; a set of boundaries coupled with power or actuation control of a tracked surgical device to ensure the end-effector only removes material from the bone within the boundaries; a set of planes or drill holes to drill pins or tunnels in the bone; or a graphically navigated set of instructions for modifying the tissue. In particular embodiments, the set of instructions is a cut-file for execution by a surgical robot to automatically modify the volume of bone, which is advantageous from an accuracy and usability perspective. The material removed by the end-effector illustratively includes subject bone, soft tissue adherent to the bone, bone cement, an exogeneous implant, or combinations thereof. The surgical plan data generated from the planning computer 416 may be transferred to the device computer 418 and/or tracking computer 420 through a wired or wireless connection in the operating room (OR); or transferred via a non-transient data storage medium (e.g., a compact disc (CD), a portable universal serial bus (USB) drive) if the planning computer 416 is located outside the OR.

The device computer 418 in some inventive embodiments is housed in the moveable base 136 and contains hardware, software, data and utilities that are preferably dedicated to the operation of the surgical robot 138. This may include surgical device control, robotic manipulator control, the processing of kinematic and inverse kinematic data, the execution of registration algorithms, the execution of calibration routines, the execution of the set of instructions (e.g., cut-files, the trajectory parameters), coordinate transformation processing, providing workflow instructions to a user, and utilizing position and orientation (POSE) data from the tracking system 406 (if present). The device computer 418 may further be programmed to provide feedback to the user to position the bones to avoid an end-effector potential collision as previously described.

The tracking system 406 (if present) may be an optical tracking system that includes two or more optical receivers 407 to detect the position of fiducial markers (e.g., retroreflective spheres, active light emitting diodes (LEDs)) uniquely arranged on rigid bodies. The fiducial markers arranged on a rigid body are collectively referred to as a tracking array (438a, 438b, 438c, 438d), where each tracking array has a unique arrangement of fiducial markers, or a unique transmitting wavelength/frequency if the markers are active LEDs. An example of an optical tracking system is described in U.S. Pat. No. 6,061,644. The tracking system 406 may be built into a surgical light, located on a boom, a stand 440, or built into the walls or ceilings of the OR. The tracking system computer 420 may include tracking hardware, software, data, and utilities to determine the POSE of objects (e.g., bones B, surgical robot 132) in a local or global coordinate frame. The POSE of the objects is collectively referred to herein as POSE data, where this POSE data may be communicated to the device computer 418 through a wired or wireless connection. Alternatively, the device computer 418 may determine the POSE data using the position of the fiducial markers detected from the optical receivers 407 directly.

The POSE data is determined using the position data detected from the optical receivers 407 and operations/processes such as image processing, image filtering, triangulation algorithms, geometric relationship processing, registration algorithms, calibration algorithms, and coordinate transformation processing.

The POSE data is used by the computing system 404 during the procedure to update the POSE and/or coordinate transforms of the bone B, the surgical plan, and the surgical robot 132 as the robot arm 138 and/or bone(s) (F, T) move during the procedure, such that the surgical robot 132 can accurately execute the surgical plan.

In specific embodiments, the surgical system 400 does not include a tracking system 206, but instead employs a mechanical digitizer arm 410, and a bone fixation system (140 or 190) with bone fixation hardware 240 to fix the bone relative to the surgical robot 138. A bone motion monitoring system may monitor bone movement when the bones are fixed to the surgical robot 132 as described in U.S. Pat. No. 5,086,401.

OTHER EMBODIMENTS

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A computerized method of collision avoidance between an end-effector and a bystander anatomy during a surgical procedure performed by a computer-assisted surgical (CAS) system, the method comprising:

registering a representation of an implant to a position of a first bone;

registering first imaging data of the bystander anatomy to a position of the bystander anatomy;

projecting a portion of the registered representation along an axis, wherein the axis represents an orientation of the end-effector when cutting at least a portion of the first bone;

determining if a projection collides with the registered first imaging data; and if the projection collides, presenting a user with options comprising at least one of: a) physically moving at least one of the first bone or the bystander anatomy; b) limiting a number cuts to the first bone by the end-effector to preclude contact between the end-effector and the bystander anatomy; or c) a combination thereof.

2. The method of claim 1, further comprising:

second imaging data of the first bone, wherein the second imaging data is registered to the position of the first bone.

3. The method of claim 2, wherein the registered representation of the implant, the registered first imaging data, the registered second imaging data, and the projected portion of the registered representation are displayed on a monitor as visual feedback or the first imaging data of the bystander anatomy is a three-dimensional (3-D) model of the bystander anatomy, and the representation of the implant is a 3-D model of the implant.

4. The method of claim 1, further comprising:

planning a position of the representation of the implant in or on the first bone based on dimensions of the first bone in pre-operative data.

5. The method of claim 1, further comprising:

moving the first bone or the bystander anatomy until the projection no longer intersects with the bystander anatomy.

6. The method of claim 1, wherein the end-effector comprises a tool having a shaft, wherein the axis represents an orientation of the shaft when removing material from the first bone, and wherein the material corresponds to the portion of the registered representation that will be received in the first bone.

7. The method of claim 1, wherein the projected portion of the registered representation is a projected cross-section of the portion of the registered representation or a projection of an entirety of the registered representation.

* * * * *